(12) United States Patent
Khillan

(10) Patent No.: US 6,281,408 B1
(45) Date of Patent: *Aug. 28, 2001

(54) EFFICIENT METHOD FOR PRODUCTION OF COMPOUND TRANSGENIC ANIMALS

(75) Inventor: Jaspal S. Khillan, Cherry Hill, NJ (US)

(73) Assignee: Thomas Jefferson University

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,036

(22) Filed: Feb. 20, 1998

(51) Int. Cl.$^7$ .............................. C12N 15/00; A01K 67/00
(52) U.S. Cl. .................................. 800/21; 800/18; 800/25
(58) Field of Search .................................. 800/21, 18, 25

(56) References Cited

U.S. PATENT DOCUMENTS 5,449,620 * 9/1995 Khillan .................................. 435/284

OTHER PUBLICATIONS

Moreadith et al. J. Mol. Med., vol. 75, pp. 208–216, 1997.*
Mullins and Mullins. J. Clin. Invest., vol. 98, pp. S38–S40, 1996.*
Torres. Current Topics in Dev. Bio., vol. 36, pp. 99–114, 1998.*
Majzoub et al. NEJM, vol. 334, pp. 904–907, Apr. 4, 1996.*
Kitsukawa et al. Development, vol. 121, pp. 4309–4318, 1995.*
Babinet et al., "Transgenic mice", (1989) *Genome*, 31:938–949.
Baribault and Kemler, Embryonic Stem Cell Culture and Gene Targeting in Transgenic Mice, (1989) *Mol. Biol. Med.*, 6(6):481–492.
Bradley et al., "Formation of germ–line chimaeras from embryo–derived teratocarcinoma cell lines", (1984) *Nature*, 309:255–256.
Camper, "Research Applications of Transgenic Mice", (1987) *Biotechniques*, 5:638–650.
Camper et al., "Implementing Transgenic and Embryonic Stem Cell Technology to Study Gene Expression, Cell–Cell Interactions and Gene Function", (1995) *Biol. of Reprod.*, 52:246–257.

Capechi, "The New Mouse Genetics: Altering the Genome by Gene Targeting", (1989) *Trends in Genet.*, 5:70–76.
Connelly et al., "The Role of Transgenic Animals in the Analysis of Various Biological Aspects of Normal and Pathologic States", (1989) *Exp. Cell Res.*, 183:257–276.
Eyestone, "Challenges and Progress in the Production of Transgenic Cattle", (1994) *Reprod. Fertil Dev.*, 6(5):647–652.
Frohman and Martin, "Cut, Paste, and Save: New Approaches to Altering Specific Genes in Mice", (1989), *Cell*, 56:145–147.
Gordon. "Transgenic Animals", (1989) *Internat. Rev. of Cytol.*, 115:171–229.
Gordon and Ruddle, "Integration and Stable Germ Line Transmission of Genes Injected into Mouse Pronuclei", (1981) *Science*, 214, 1244–1246.
Iannaccone et al. "Pluripotent Embryonic Stem Cells from the Rat Are Capable of Producing Chimeras", (1994) *Dev. Biol.*, 163:288–292.
Liggitt and Reddington, "Transgenic animals in the evaluation of compound efficacy and toxicity: will they be as useful as they are novel?", (1992) *Xenobiotica*, 22(9–10):1043–1054.
Palmiter and Brinster, "Germ–Line Transformation of Mice", (1986) *Ann. Rev. of Genet.*, 20:465–499.
Scangos and Bieberich, "Gene Transfer Into Mice", (1987) *Advances in Genet.*, 24:285–322.
Thompson et al., "Germ Line Transmission and Expression of a Corrected HPRT Gene Produced by Gene Targeting in Embryonic Stem Cells", (1989) *Cell*, 56:313–321.
Williams et al., "Embryonic stem cells as targets for gene transfer: a new approach to molecular manipulation of the murine hematopoietic system", (1990) *Bone Marrow Transplant.*, 5:141–144.

* cited by examiner

Primary Examiner—Deborah J. R. Clark
Assistant Examiner—Michael C. Wilson
(74) Attorney, Agent, or Firm—Janet B. Smith

(57) ABSTRACT

A method of producing compound transgenic animals by co-culturing embryonic stem cells with a morula is provided.

3 Claims, No Drawings

EFFICIENT METHOD FOR PRODUCTION OF COMPOUND TRANSGENIC ANIMALS

BACKGROUND OF THE INVENTION

The introduction of foreign genes into the germline of recipient animals was first achieved in the early 1980's (Camper (1987) *Biotechniques*, 5:638–650; Bradley et al. (1984) *Nature*, 309:255–256; Palmiter and Brinster (1986) *Ann. Rev. of Genet.*, 20:465–499). These types of procedures relied on the microinjection of cloned DNA into the pronuclei of fertilized eggs with subsequent transfer of the eggs into oviducts of pseudopregnant females for gestation (Gordon and Ruddle (1981) *Science*, 214, 1244–1246). Approximately one to a hundred copies of the microinjected DNA integrate randomly into the genome, usually at a single site, in a fraction of the animals born. These transgenic founder animals usually carry the foreign gene in both somatic cells and germline cells, allowing passage of the transgene to progeny in a Mendelian manner.

The creation of transgenic animals by this and similar methods has proven invaluable as a tool to introduce new and rare genetic characteristics into existing breeds of mammals (Babinet et al. (1989) *Genome*, 31:938–949; Connelly et al. (1989) *Exp. Cell Res.*, 183:257–276; Scangos and Bieberich (1987) *Advances in Genet.*, 24:285–322). For example, using appropriate regulatory promoter sequences the expression of genes can be directed to the specific tissues or biofluids such as milk or blood of the transgenic animals. Additionally, genes for the proteins of biomedical importance may be fused downstream of specific promoter to express their products either in milk or blood. These proteins can then be isolated from the fluids by common techniques known to those of skill in the art, on a routine basis. Large transgenic species such as cow, goat and sheep may potentially be a valuable reservoir of great quantities of the transgenic protein because of the amount of milk and blood present in these animals. The transgenic animals act as bioreactors or factories for the production of designed, species-specific peptides or proteins or even cells.

However, the generation of these larger species of transgenic animals present some unique challenges (Eyestone (1994) *Reprod. Fertil Dev.*, 6 (5):647–652). In general, the efficiency of gene integration is very poor in these animals. Frequencies of approximately 0.1% for cow and <1.0% for sheep have been reported. Additionally, the survival of microinjected zygotes is low; only 15% in vivo-derived develop into morulae and blastocysts and, of these, only about 18% yield live animals. Thus, more than 1000 zygotes must be injected to produce a single transgenic animal. In addition, the gestation period for large mammals is generally long. These kinds of conditions require that large colonies of donor and recipient animals be maintained. Therefore, given current technology, this type of approach seems logistically and financially prohibitive to implement.

More recently, embryonic stem (ES) cells have been utilized in biotechnological applications such as targeted gene disruption and creation of transgenic mice (Beribault and Kemler (1989) *Mol. Biol. Med.*, 6(6):481–492; Iannaccone et al. (1994) *Dev. Biol.*, 163:288–292; Camper et al. (1995) *Biol. of Reprod.*, 52:246–257). ES cells are pluripotent cells established from normal embryos, and in particular blastocysts. These cells can be cultured and manipulated in vitro and will resume normal development when implanted into blastocysts from foster mothers. Microinjection, electroporation, and retroviral infection have all been successfully used to introduce foreign genes into these cells (Frohman and Martin (1989), (1989) *Cell*, 56:145–147; and Gordon (1989) *Internat. Rev. of Cytol.*, 115:171–229). The use of gene knockout animals generated from ES cells has been important for studying the hormonal and developmental control of gene expression, for producing animal models of cancer and other diseases and testing the efficacy of gene therapy, and for looking at cell-cell interactions and cell lineage relationships (Camper et al. (1995) *Biol. of Reprod.*, 52:246–257).

One advantage of the ES based method for generating transgenic animals is that cells positive for the presence of the transferred foreign genetic material may be selected for before generation of the transgenic animal. Thus, cells in which homologous recombination of the gene has occurred may be used to establish the transgenic cell line. This propensity towards homologous recombination has been used in creating "knock-outs" or inactivation of endogenous genes as well as to replace defective genes (Capechi (1989) *Trends in Genet.*, 5:70–76; Thompson et al. (1989) *Cell*, 56:313–321; and Williams et al. (1990) *Bone Marrow Transplant.*, 5:141–144). Mice generated from ES-inoculated blastocysts are chimeric in somatic and germ cells for the selected, novel trait. Inbreeding of heterozygotes permits generation of homozygotes and phenotypic expression of the trait.

A method has now been developed utilizing embryonic stem cells to efficiently generate transgenic animals that highly express an integrated foreign gene. Using this method, chimeric animals are produced that contain ES cells with different integrations of exogenous DNA. Since this method does not rely on homologous recombination, what is produced are compound transgenic animals. The germline of these animals represents a potential source to transmit each independent integration separately to its progeny. Therefore, using the techniques of in vitro fertilization and artificial insemination, the method of the present invention can be used to efficiently and inexpensively create a large number of high expressing animals within a relatively short period of time.

SUMMARY OF THE INVENTION

An object of the present invention is to provide a method of producing compound transgenic animals utilizing embryonic stem cells in a one step co-culture of the embryonic stem cells with a blastocyst or morula.

DETAILED DESCRIPTION OF THE INVENTION

Over the past 15 years, transgenic animals have proven to be valuable resources for a variety of biological applications. These include uses such as; studying hormonally influenced gene expression, cell-cell interactions and gene function employing gene knock-out and/or replacement strategies (Camper et al. (1995) *Biol. of Reprod.*, 52:246–257). These animals can also be used as models for human diseases in which immune and metabolic pathways may be dissected as well as a means to explore mechanisms of development, mutagenesis, and teratogenesis. In addition, transgenic animals can be used in drug development to evaluate compound efficacy and toxicity as well as in the production of biologically valuable proteins (Liggitt and Reddington (1992) *Xenobiotica*, 22(9–10):1043–1054).

The most common method to generate transgenic animals is to microinject the gene of interest into one of the pronuclei of a newly fertilized embryo. The microinjected embryo is then implanted into a pseudopregnant recipient to obtain live newborns. However, this method both tedious and unpredictable. It also requires highly specialized skills of microinjection.

Though this method is the most successful, it has several limitations. First, the method utilizes only one cell stage embryos for microinjection which is generally limiting especially in the case of large animals. Further, microinjection is performed at the one cell stage which is more vulnerable to damage. Therefore many of the embryos fail to survive. Further, in larger species it is generally difficult to obtain large numbers of synchronized one cell embryos. In addition, one cell embryos of the large species are pigmented thereby making it difficult to visualize the pronuclei for microinjection. Finally, each microinjection generally leads to only one transgenic animal, therefore microinjection of several embryos is required to obtain a transgenic animal that expresses transgenes at the economically viable level.

In the present invention, embryonic stem cells are used in a mixed cell co-culture with a morula to generate transgenic animals. In a preferred embodiment, foreign genetic material is introduced into the embryonic stem cells prior to co-culturing. For example, in one embodiment a DNA clone is electroporated into ES cells. Other methods for introducing exogenous DNA into cells such as microinjection or use of retroviruses can also be used. ES cells transfected in this manner are selected for integrations of the gene via a selection marker such as neomycin at concentrations up to 500 $\mu$g/ml, propagated, and cultured further for expansion. The ES cells are cultured on mitotically inactive primary feeder cells. The cells for co-culture are harvested by treatment with trypsin-EDTA. The cells are washed two times with Brinster's medium and resuspended in the same medium with 10 mg/ml BSA at a concentration of 1–2×10$^5$ cells/ml.

These cells represent a pool in which different cell populations may have different integration of exogenous DNA. Microinjection of such pools of cells with independent integrations into the cavity of a blastocyst, or in a preferred embodiment, co-culturing the ES cells with a morula, produces a chimeric animal containing ES cells with several integrations thus representing a compound transgenic animal. The germline of the animals thus represents a potential source for transmitting each independent integration separately to its progeny. Accordingly, the same chimeric parent may produce several progeny with different integrations. Each such progeny represents an independent founder of a line of animals from which the high expressing lines can be selected and propagated.

To produce these animals, approximately 100 $\mu$l of the cell suspension is transferred onto the microwells of the co-culture plate. The cells are covered with paraffin oil and allowed to settle for approximately 10 minutes. Morulas are isolated by flushing the uterine horns of pregnant females. The zona pellucida is removed by treating with the acidic Tyrode solution. The denuded embryos are then transferred to the microwells with one embryo being placed in each microwell on top of the ES cells. The plates are then cultured overnight. The following day, the embryo develops into a blastocyst. Blastocysts are collected from the wells, washed with fresh medium and transferred into the uterine horn of 2.5 day pseudopregnant females. The pups are born after about 16–17 days.

By using the techniques of in vitro fertilization and artificial insemination, the method of the present invention can be used to create a large number of high expressing animals within a much shorter time. Further, with the availability of ES cells from different species the method of the present invention can be used with high efficiency to create transgenic large animals thus saving time and resources. Another major advantage in using the method of the present invention is that it requires only morulae and blastocyst embryos which can be collected with relative ease from both small and large species by uterine flushing. In addition, the transgenic ES cells may be tested in tissue culture for the expression of genes before preparing chimeric animals. Using only the cells that express the gene of interest can be highly advantageous in obtaining transgenic animals which will most probably express the gene which is not possible by the conventional microinjection technique. By using a high concentration (up to 500 $\mu$g/ml) of selection drug G418 for the neomycin resistance gene, integration sites that are low expressors are eliminated. Biologically relevant proteins may be produced in chimeric progeny by incorporating a secretory signal into the transgene DNA such that the protein may be secreted into easily extractable fluids like blood or milk.

Using the method of the present invention, seven high degree chimeras were prepared by the co-culture of a mixture of 4 ES cell clones with independent integration of the neomycin gene with morulae. The chimeras displayed 80–100% ES cell contribution of ES cells by coat color. Three chimeric animals were crossed with wild type animals to produce 16 pups. Of these 16, PCR analysis revealed that 4 pups carried the neomycin gene in their genome.

Cells from the positive animals were cultures on 60 mm petridishes. At confluency the cells were treated with G418 at 300 $\mu$g/ml and 500 $\mu$g/ml. The cells from non-transgenic pups died after G418 treatment whereas the cells from transgenic pups survived at both concentrations proving further that the site of integration is fully active in the progeny of chimeric animals.

This method may be used to quickly and efficiently generate a wide assortment of transgenic animals harboring a gene cassette (necessary promoter regions plus the open reading frame of interest). Because this method relies on creation of a compound transgenic animal, i.e random insertions of the gene in the chromosome of the animals, as opposed to homologous recombination of the DNA at a particular site, the percentage of high expressing progeny (obtained from crosses using chimeric parents) is much higher overall.

The following nonlimiting examples are provided to further illustrate the present invention.

EXAMPLES

Example 1

Electroporation of DNA

A DNA clone which contains the neomycin resistance gene was electroporated into the embryonic stem cells. Cells were selected by G418 and individual clones were picked. The clones were propagated separately and at confluency, cells were divided into equal halves. One half of the cells were cultured further for the expansion of the cells and the other half was used to isolate DNA.

Example 2

Southern Analysis of the ES Clones

The isolated DNA was digested with BamHI enzyme and analyzed by Southern blot using a p$^{32}$ labeled probe specific for the neomycin gene. Altogether nine clones were propagated. A Southern analysis of five individual clones showed that each clone presented a unique digestion pattern indicating that the DNA integrated at unique sites in each independent clone.

Example 3

Preparation of Chimeric Animals

Cells from one to four clones were pooled and propagated as a mixed cells preparation. The mixed cells were used to prepare chimeric animals. High degree chimeras were prepared by co-culture of ES cells with the morulae isolated from the FVB/N strain of mice. These mice displayed 80–100% chimerism by coat color.

Additional chimeras were prepared by co-culture of mixed ES cells with morulae isolated from the C57BL6 strain of mice. These chimeras displayed almost 100% ES cell contribution by coat color. At the age of maturity animals are crossed with the wild type to check for germline transmission.

Example 4

Germline Transmission of the Gene

Analysis of transmission of the transgene to progeny is performed by crossing FVB/N chimeras with wild type FVB/N females. Pups produced in the cross are screened for the presence of the neomycin gene by polymerase chain reaction (PCR) using primers specific for the neomycin gene, neo2-neo3.

Using this method, four pups amplified a 330 bp band specific for the neomycin gene suggesting that the chimeras have ES integrated into their germline. To investigate the nature of integration in each of the progeny the DNA is isolated and analyzed by Southern blots.

What is claimed is:

1. A method of producing a compound chimeric mouse, comprising:
   (a) obtaining mouse embryonic stem (ES) cells whose genomes' comprise a construct comprising a nucleic acid sequence encoding a marker gene and a gene of interest each of which is operatively linked to a promoter;
   (b) selecting said ES cells of (a) that functionally express said marker gene;
   (c) cloning said ES cells of (b) to obtain individual ES cell clones;
   (d) analyzing the site of integration of each of said individual ES cell clones of (c);
   (e) selecting at least two of said individual ES cell clones of (d) with different sites of integration;
   (f) mixing said individual ES cell clones selected in (e) to form a mixed pool of ES cell clones with different integration sites;
   (g) co-culturing said mixed pool of ES cell clones with a mouse morula having a zona pellucida removed such that compound chimeric mouse embryos are formed;
   (h) transferring said compound chimeric mouse embryos to a pseudopregnant female; and
   (i) obtaining a compound chimeric mouse comprising cells that express said gene of interest to detectable levels.

2. The method of claim 1, wherein said marker gene is a neomycin resistance gene.

3. A method of producing transgenic mice, comprising:
   (a) crossing a compound chimeric mouse comprising cells that express a gene of interest to detectable levels obtained by the method of claim 1 with a wild-type mouse; and
   (b) obtaining said transgenic mice whose genomes comprise a nucleic acid sequence encoding a marker gene and a gene of interest each of which is operatively linked to a promoter, wherein said transgenic mice comprise cells that express the gene of interest to detectable levels.

* * * * *